United States Patent
Lapierre et al.

[19]
[11] Patent Number: 6,114,179
[45] Date of Patent: *Sep. 5, 2000

[54] METHOD AND TEST KIT FOR DETECTING ANTIGENS AND/OR ANTIBODIES

[75] Inventors: Yves Lapierre, Oullins, France; Dieter Josef, Fribourg, Switzerland; Jean Adam, Meyriez, Switzerland; Susanne Greber-Widmer, Herrenschwanden, Switzerland

[73] Assignee: Stiftung fur Diagnostische Forschung, Murten, Switzerland

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/094,578

[22] Filed: Jun. 12, 1998

Related U.S. Application Data

[62] Division of application No. 08/579,145, Dec. 27, 1995, Pat. No. 5,863,802, which is a division of application No. 08/283,552, Aug. 1, 1994, Pat. No. 5,512,432, which is a continuation of application No. 07/969,532, Oct. 30, 1992, Pat. No. 5,338,689, which is a continuation of application No. 07/684,459, Apr. 11, 1991, abandoned, which is a continuation of application No. 07/122,152, Nov. 17, 1987, abandoned.

[30] Foreign Application Priority Data

Aug. 24, 1987 [CH] Switzerland .............................. 3240/87

[51] Int. Cl.[7] ...................... G01N 33/536; G01N 33/537; G01N 33/538; G01N 33/543

[52] U.S. Cl. ................ 436/518; 422/58; 422/61; 422/72; 422/73; 422/68.1; 422/99; 422/102; 422/104; 435/5; 435/7.2; 435/7.21; 435/7.25; 435/7.32; 435/975; 436/164; 436/165; 436/514; 436/519; 436/520; 436/524; 436/527; 436/528; 436/529; 436/534; 436/536; 436/538; 436/541; 436/805; 436/808; 436/809; 436/824

[58] Field of Search ................... 422/58, 61, 72, 422/73, 68.1, 99, 102, 104; 435/5, 7.2, 7.21, 7.25, 7.32, 7.9, 975; 436/164, 165, 514, 518, 519, 520, 524, 527, 528, 529, 534, 536, 538, 541, 805, 808, 809, 824

[56] References Cited

U.S. PATENT DOCUMENTS

| | | | |
|---|---|---|---|
| 3,492,396 | 1/1970 | Dalton et al. | 422/58 |
| 3,718,133 | 2/1973 | Perry et al. | 128/272 |
| 3,876,376 | 4/1975 | Bauman et al. | 424/12 |
| 5,338,689 | 8/1994 | Yves et al. | 436/518 |
| 5,460,940 | 10/1995 | Yves et al. | 435/5 |
| 5,512,432 | 4/1996 | LaPierre et al. | 435/5 |

FOREIGN PATENT DOCUMENTS 8502010  2/1985  France.

Primary Examiner—Christopher L. Chin
Attorney, Agent, or Firm—Arent Fox Kintner Plotkin & Kahn

[57] ABSTRACT

A suspension of inert particles is prepared in an aqueous solution, to which an antibody or an antigen and a carrier-bound antigen or antibody, respectively, are added in any desired order. After centrifuging, the positive, weakly positive, or negative reaction can easily be recognized on the basis of a simple pattern.

30 Claims, 2 Drawing Sheets

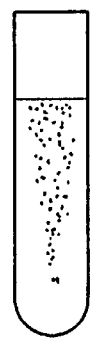
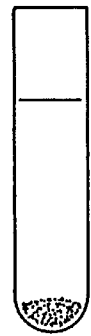
FIG. 1(a)    FIG. 1(b)    FIG. 1(c)
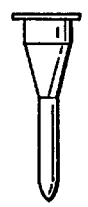
FIG. 2(a)    FIG. 2(b)
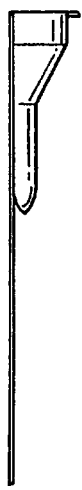
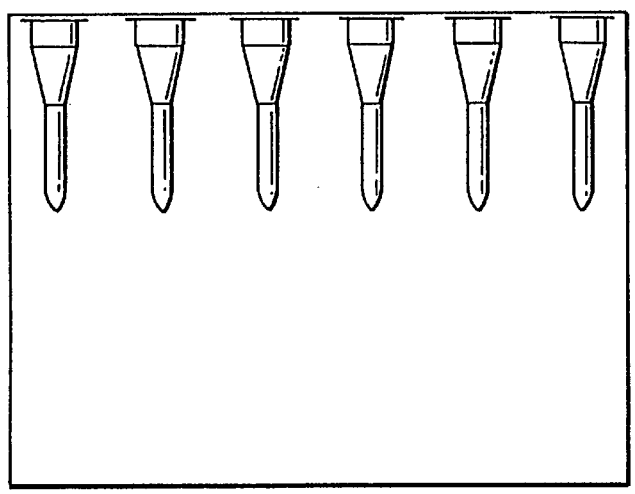
FIG. 3a    FIG. 3b
FIG. 4(a)    FIG. 4(b)    FIG. 4(c)

METHOD AND TEST KIT FOR DETECTING ANTIGENS AND/OR ANTIBODIES

This is a divisional application of U.S. Ser. No. 08/579,145, filed Dec. 27, 1995 now U.S. Pat. No. 5,863,802, which was a divisional of U.S. Ser. No. 08/283,552 filed Aug. 1, 1994, now U.S. Pat. No. 5,512,432, which is a continuation of Ser. No. 07/969,532 filed on Oct. 30, 1992, now U.S. Pat. No. 5,338,689, which is a continuation of Ser. No. 07/684,459 filed Apr. 11, 1991, abandoned, which is a continuation of Ser. No. 07/122,152, filed Nov. 11, 1987, abandoned.

This invention relates to biological test methods, and more particularly to a method of detecting antibodies or antigens, of the type wherein complexes of carrier-bound antibodies with antigens or of carrier-bound antigens with antibodies in an aqueous medium are made optically visible, using inert particles such as polyacrylamide gel particles. The invention further relates to test kits for detecting antigens and/or antibodies according to the aforementioned method.

Carrier-bound antigens and antibodies are routinely utilized for a multitude of analytical determinations. In this connection, a distinction is generally made between two principles:

(a) The antigen or antibody is bound to a sold carrier, such as small glass or plastic test tubes, glass or plastic beads, glass or plastic plates, paper, etc., and the liquid containing the antibody or antigen to be identified is added. If, after a certain reaction time, the latter react with the bound antigen or antibody, they are bound to the carrier and can, at least by means of a further reaction, be made measurable. As a rule, this takes place by labeling the antibody or antigen with radioactive, fluorescent, or enzymatically active tagging substances. A drawback of this method is that it is trouble-prone. Since washing is necessary after each reaction, insufficient washing or insufficient removal of the washing solution can falsify the results. Moreover, this method is hardly applicable to natural, carrier-bound antigens on erythrocytes, leukocytes, platelets, and other natural cells because of their size.

(b) Another principal method consists in binding the antigen or antibody to small particles such as latex or erythrocytes. After a certain reaction time with the antibody or antigen to be identified, the evaluation takes place on the basis of the agglutination pattern. Unlike the method described under (a) above, antigens and antibodies on erythrocytes, leukocytes, or platelets can be identified by this method. Drawbacks of this method are that, especially in a weak concentration, it is hard to differentiate between agglutinated and non-agglutinated (free) particles. Moreover, free particles can easily be adsorbed on the reaction vessel or the agglutination pattern mechanically destroyed. A further source of error resides in the possible adhesion of free particles to one another, thus simulating an agglutination. All these eventualities can lead to a false evaluation.

European Published Application No. 0 039 195 describes an antibody-detection method wherein erythrocytes in negatively charged form are used in an isotonic solution of low ionic strength. A polymer in solution is added as an aid to agglutination. The agglutination is observed visually, preferably under a microscope. The agglutinate can be dissociated again by adding a solution of citrate and sugar.

It is an object of this invention to provide an improved method of detecting antibodies or antigens which is simpler than the prior art methods and free of their drawbacks.

Another object of this invention is to provide such a method in which readings can be taken easily and reliably.

To this end, in the method according to the present invention, a solution containing an antibody or an antigen is brought into contact with a carrier-bound antigen or antibody, respectively, a slurry or suspension of inert particles being added before, during, or after this reaction; upon formation of an antigen-antibody complex, the latter lying upon the sediment of the inert particles in the strongly positive case and being present within the inert particles in the weakly positive case; and in the absence of an antigen-antibody complex, i.e., in the negative case, the carrier-bound antibodies or antigens lying beneath the inert particles sediment.

The test kit according to the present invention contains at least one reaction vessel, inert particles, and one carrier-bound antibody and/or antigen per reaction vessel.

The chemical composition of the inert particles used in the method is not critical. The term "inert" is intended to mean that the particles must not enter into any unspecific reactions with the antigens or antibodies. Preferably, such inert porous particles as are available in commerce for liquid or gas chromatography will be used. These are products on the basis of cross-linked polymers, such as agarose, polyacrylamide, polydextran, or styrene-divinylbenzene polymers (e.g., "Sephadex, " "Sepharose," or "Sephacryl," sold by Pharmacia AB, Uppsala, Sweden; or "Bio-Gel," sold by Bio-Rad Laboratories, Richmond, Calif.). Porous glass or silica gel also enters into consideration. The particle size is preferably from 10–200 microns. Those skilled in the art can determine by means of simple preliminary tests whether the particles are usable for a certain method of determination. As in the case of the above-mentioned inert particles, the type of carrier for the antigen or antibody is also not critical. For visual or optical-automatic measuring methods, it should be colored by nature (e.g., erythrocytes). However, the carriers may also be tagged by means of a stain (e.g., latex, polymerized agarose). Other marking systems also enter into consideration, such as isotope, fluorescent, or enzyme labelling. These naturally require an appropriate measuring method. Moreover, the carriers are preferably likewise in particle form, the antigens or antibodies being bound to their surfaces.

The antigens and antibodies are preferably bound to these particles by chemical bonding, the type of bonding not being critical. Certain antigens, such as those of erythrocytes and platelets, already exist bound to these carriers. Leukocytes and platelets may be stained by known methods, if need be.

In the case of leukocytes or platelets, the inert particles may alternatively be stained. In that event, the reading zone is whitish, and the inert particles are colored.

According to the method of the present invention, it is possible to determine the free antigens or antibodies, certain carrier-bound antibodies or antigens, respectively, having to be given. Conversely, the carrier-bound antigens or antibodies may also be determined, the free antigens or antibodies, respectively, having to be given. The reaction vessels used for carrying out the method are, as a rule, small test tubes or microtiter plates of glass or plastic. The material is not critical. The small test tubes may be either rounded or pointed, the shape being chosen as a function of the reading technique and the technical separation method and the quantity of material.

For carrying out the method of the present invention, small tubes or microreaction vessels are preferably used. Any desired number of these may, for example, be arranged side by side on a card. There may be an additional vessel, e.g., for preparing a test dilution or test suspension. The vessels and cards may be of plastic, such as PVC/PVDC, PET, or polystyrene. The vessels may, for instance, be made by the blister method, by a welding process, or by gluing. The vessels may contain the inert particles or industrially prepared reaction solutions. Since the invented method preferably includes a centrifuging step, special, suitable centrifuge heads must be used for the tubes or the cards with the containers. With one advantageous centrifuge head, at least 12 cards having, for example, six reaction vessels can be centrifuged simultaneously. In this case, 72 tests can be carried out parallel to one another.

Although sedimentation can be brought about by allowing the vessels to stand and taking advantage of the force of gravity, it is more advantageous to use the centrifuging method since the desire sedimentation can be achieved after only a short time. The optimum conditions (centrifuging time and number of g) must be ascertained for each analysis system since the specific gravity, size, shape, deformability, and stability of the carrier-bound antigen-antibody complex, of the non-complexed, carrier-bound antibodies and antigens, and of the inert particles have an influence which is difficult to calculate.

Certain aspects of the invention will now be described in detail with reference to the accompanying drawings, in which:

FIGS. 1(a)–(c) are diagrammatic elevations of three test tubes showing the patterns occurring in positive, weakly positive, and negative reactions, FIGS. 2(a)–2(b) are a side elevation and a front elevation of a typical microtube suitable for affixing to a card, FIGS. 3a and 3b are a side elevation and a front elevation, respectively, of a card with six small test tubes as in FIG. 2, FIGS. 4(a)–4(c) are a diagram of the way in which the test is carried out, and FIGS. 5, 6, and 7 are elevations of test cards for typical routine clinical tests.

Theoretically, the method according to the present invention can be used to test a sample of liquid for an antigen or an antibody which is specific to a known antibody or antigen, respectively. Either the known antigen or antibody, or the unknown antibody or antigen, must be bound to a carrier, e.g., an erythrocyte. The method of detection is based upon the realization that carrier-bound antigens and antibodies have different centrifugation properties from carrier-bound antigen-antibody complexes. If an antigen-antibody complex on a carrier is centrifuged together with a suspended, inert carrier material, the carrier-bound complex lies on the inert particles. If no reaction has taken place, only a free, carrier-bound antigen or antibody is in the test tube with the inert, suspended material. After centrifuging, this antigen or antibody is situated beneath the layer of inert particles. In this way, the positive or negative antibody reaction can plainly be read visually. It is also possible to automate this reaction. Weakly positive reactions may also occur, in which case the carrier-bound antigen-antibody complex is situated within the layer of inert particles.

A pattern of a positive reaction is shown in FIG. 1(a). If the reaction is only weakly positive, i.e., if only a few antigen-antibody complexes are formed, the antibody can be detected in the upper part of the inert particles in the centrifuge glass; cf. FIG. 1(b). If, on the contrary, there is no antigen-antibody complex but only a carrier-bound, free antigen or antibody, the latter is deposited beneath the inert particles after centrifuging. This is shown in FIG. 1(c).

As already mentioned, although various types of reaction vessels may be used, one such as is depicted in FIG. 2 is preferred. A side view is shown on the left, and a front view on the right. This small tube is covered, thus making it possible for certain industrially manufactured reagents to be supplied directly in the small test tube. The test tube is suitable for affixing to a card, which may hold several tubes, e.g., as shown in FIG. 3, where there are six small test tubes. FIG. 3a is a side view of the test card, while FIG. 3b is a front view. By means of this arrangement, a direct comparison of parallel tests is made possible.

The test card may be made in various ways. For example, small tubes may be glued to a card or may form an integral part of the card, in the manner of blister packaging. A mixture of inert particles and antibodies or antigens may be hermetically enclosed in these tubes in a predetermined quantity by the manufacturer, in which case the tubes may be sealed by means of a welded-on film. Test kits manufactured in this way are easily handled and may be used in an automatic analysis method. In this case, the pipetting of specimens, identfication, automatic reading, evaluation, print-out, etc., is controlled by means of electronic data-processing. A further advantage is that only very small specimens are necessary. For instance, with 10–50 $\mu$l of blood, all clinically relevant antigens can be detected with small amounts of reagents. Micro-batches are particularly important in the case of substances which cannot be prepared synthetically and are available only in limited quantities; e.g., with 1 ml of the Rh antibody C, 20 antigen determinations can be carried out by a conventional method, whereas 1000 determinations are possible with the present method. If the test system is appropriately prepared, the determinations are so easy to carry out, and the results so plainly readable, that the test can even be carried out by auxiliary medical personnel.

Since no special laboratories are necessary, the interval between diagnosis and the start of therapy can be considerably reduced.

The invention will now be explained in more detail by means of the following examples.

I. Blood Group Antigens (ABO System)

EXAMPLE 1

A Antigen
(a) Preparation of Inert Particles Suspension

Five ml of "Sephacryl," S200 Gel (Pharmacia) is washed twice in saline solution. After centrifuging (5 min., 1250 g), the supernatant is discarded, and the sediment is filled up to 4.5 ml with isotonic imidazol buffer (0.014 mol/l of imidazol 0.85% NaCl), pH 7.6.
(b) Addition of Antibody Five-tenths ml of anti-A is added to 4.5 ml of the above suspension. The suspension is mixed well and is ready for use in this form.
(c) Preparation of Reaction Vessels The above antibody suspension is placed in polyethylene micro-tubes (ET-29MM, sold by Milian SA, Geneva, Switzerland), 100 $\mu$l in each tube. The inert particles settle to the bottom of the tube within a few minutes.
(d) Test Procedure Twenty $\mu$l of an app. 4% erythrocyte suspension of the unknown blood specimens in isotonic imidazol buffer, pH 7.0 (one part blood to nine parts buffer) is placed in the reaction vessel filled with the antibody suspension and centrifuged for 10 min. at app. 100 g (Digifuge GL 122 089 centrifuge, 800 rpm, sold by Heraeus, Hanau, West Germany).

(e) Evaluation

If the tested blood belongs to blood group A ($A_1$ or $A_2$), the antigen-antibody complex lies upon the inert particles (FIG. 1a). If it belongs to the rare A subgroups $A_3$ or $A_x$, the complex is distributed between the inert particles (FIG. 1b). If the blood belongs to groups B or O, no agglutination can take place, and the erythrocytes collect at the bottom of the tube beneath the inert particles after centrifugation (cf. Table 1).

TABLE 1

| Blood Group | $A_1/A_2/A_1B/A_2B$ | $A_3/A_3B/A_x$ | B/O |
|---|---|---|---|
| Test | Positive (FIG. 1a) | Weakly positive (FIG. 1b) | Negative (FIG. 1c) |

Completely analogously to Example 1, the B antigen is determined with anti-B instead of anti-A. The H antigen can be detected with H lectin. $A_1$ is distinguished from $A_2$ by means of $A_1$ lectin. Example 1 admits of a multitude of variations of the inert particles, the buffer used, the reaction vessels, the centrifugation time, and the number of g. The origin of the antibodies—whether human, animal, or vegetable, whether polyclonal or monoclonal—is unimportant, provided the variations do not change the reaction image (FIG. 4).

II. Rh-System Blood Groups (D, Du, C, E, c, e, Cw)

EXAMPLE 2

E Antigen

The preparation of the reaction vessels (steps a–c) is as in Example 1. Instead of anti-A, anti-E is used, for example.

(d) Test Procedure

Step (d) of Example 1 is modified in that an enzyme solution ("DiaBrom," sold by DiaMed AG, Murten, Switzerland) is used instead of the imidazol buffer. It is known that concealed Rh antigens can be exposed thereby. Fifty μl of blood is suspended in 0.5 ml of enzyme solution. After app. 5 min., 20 μl of this suspension is placed in the reaction vessel prepared as in steps (a)–(c) of Example 1 and centrifuged for 10 min. at 100 g.

(e) Evaluation

If the blood specimen contains antigen E, the antigen-antibody complex rests upon the inert particles (Table 2). Is antigen E not present, the erythrocytes collect under the inert particles.

TABLE 2

| | E antigen present | E antigent absent |
|---|---|---|
| Test | Positive (FIG. 1a) | Negative (FIG. 1c) |

The other Rh antigens can be determined completely analogously by means of the appropriate antisera. The clinically important D-variant Du can be differentiated by varying the concentration of anti-D.

III. Antibodies

EXAMPLE 3

Reverse Test (Isoagglutinins)

The reaction vessels are prepared as in Example 1 (steps a–c), except that imidazol buffer is substituted for the antibody.

(d) Test Procedure

Since antibodies are to be identified in this example, erythrocytes with known antigens are used, e.g., A, B, and O test erythrocytes. These are suspended in the known LISS solution (50 μl of blood and 2.0 ml of LISS). Fifty μl of serum or plasma of the unknown blood specimen are placed in each of three identically filled reaction vessels. One hundred μl of the A-cell suspension in LISS is added to the first tube, 100 μl of the B-cell suspension to the second tube, and 100 μl of the O-cell suspension to the third tube. As in Examples 1 and 2, the suspensions are centrifuged for 10 min. at 100 g.

(e) Evaluation

If the unknown specimen contains anti-A, the first tube is positive, the second and third tubes negative (Table 3).

TABLE 3

| | A cells | B cells | O cells |
|---|---|---|---|
| Test | Positive (FIG. 1a) | Negative (FIG. 1c) | Negative (FIG. 1c) |

If the specimen contains anti-B, the second tube is positive, the first and third negative. If the third tube is positive, and the first and second are positive or negative, the specimen contains antibodies which are not anti-A or anti-B but directed to other antigens which lie on the O cells. In this event, further investigation is necessary

EXAMPLE 4

Antibody Screening Procedure (Coombs Test)

The preparation of the reaction vessels is as in Examples 1–3, except that Coombs serum (DiaMed AG) is added to the inert particles suspension. As is well known, Coombs serum consists of anti-human-IgG and anti-complement C3 (C3b, C3d), as well as anti-IgM and anti-IgA, and is used for detecting and identifying, in serum from patients, antibodies directed to erythrocyte antigens. It is expedient first to carry out an antibody screening procedure in which O erythrocytes having a known antigen for clinically relevant antibodies are used. If the result is positive, identification by means of a cell panel takes place.

Test Procedure

Fifty μl of serum or plasma from the patient is placed in each well or funnel of one or more identical reaction vessels filled with Coombs-serum suspension. One hundred μl of the O-cell suspension (50 μl of blood in 2.0 ml of LISS) is added. The mixture is incubated for from 10–20 min. at 37° C., at room temperature, or at from 2–8° C., depending upon the antibody sought, and centrifuged for 10 min. at 100 g. Reading takes place as in the previous examples.

If the specimen contains an antibody against one or more erythrocyte antigens, the positive pattern of FIG. 1(a) appears. With weaker antibodies, the pattern is as in FIG. 1(b). Analogous to the above test procedure, the antibody discovered may be identified by means of a cell panel containing various antigens (e.g., products obtainable in commerce from Ortho, Raritan, N.J.; Dade, Baxter, Miami, Fla.; and DiaMed).

IV. Blood-Typing on a Card

EXAMPLE 5

Blood Group A, $B_1B_1$ (CCDee), Kell Negative, Control Negative

Typing can be done individually in small tubes, on microtiter plates, or on cards. In this example, blood-typing on cards designed for determining a patient's blood group is described. The preparation of the reaction vessels taken place as described above. The cards are shown in FIGS. 5–7.

V. Determination of Free Antigens or Antibodies Not Belonging to Blood-Group Systems The reactions in Examples 1–5, in which the antigen is bound to the erythrocytes by its nature, can be applied to free antigens or antibodies by binding the respective antibodies or antigens to fixed erythrocytes or other particles by known methods.

EXAMPLE 6

Rheumatoid Factor Test (a) Preparation of erythrocytes:

Five ml of goat's blood in 0.011 mol citrate buffer, pH 6, is washed three times in saline solution. The sediment is suspended with 5 ml of saline solution, mixed with 0.5 ml of 30% glutaraldehyde solution (E. Merck AG, Darmstadt, West Germany), and allowed to react for 24 hrs. at room temperature with stirring. The sediment is washed three times in saline solution, mixed with 0.5 ml of rabbit IgG (10 mg/ml), and incubated for 24 hrs. at room temperature with stirring. After washing three times in saline solution, an app. 40% suspension of the loaded erythrocytes in imidazol buffer is prepared.

(b) Test Procedure

The reaction vessels are prepared as in Example 3. An app. 4% erythrocyte suspension is prepared with imidazol buffer. As in Example 4, 50 μl of serum from the patient is placed in the well of the test tube, and 20 μl of the 4% erythrocyte suspension is added. After about 10 min. incubation at room temperature, centrifuging takes place as usual. If the serum contains rheumatoid factors, the reaction pattern of FIG. 1(a) or (b) appears. If it is desired to ascertain the titer, the test is repeated with serum diluted accordingly (0.9% NaCl).

The foregoing test is naturally not limited to the rheumatoid factors; for example, hepatitis antigens could be detected after coupling of HBsAg antibodies. By coupling inactivated HIV virus or synthetically produced proteins thereof to the erythrocytes, HIV antibodies can likewise be easily detected.

Based upon these examples, it is immediately apparent that other proteins, viruses, or bacteria, or antibodies thereof, can easily be determined by the same method.

What is claimed is:

1. A method of detecting a target antibody or antigen, the method comprising:
    providing a microreaction vessel containing a slurry or suspension of particles and a known target or binding partner thereto, wherein the vessel has an upper portion having a sample receiving end and a lower portion having a closed end, the upper portion having a greater diameter or width than the lower portion, with a transition portion situated between the upper portion and the lower portion;
    adding to the vessel a solution containing an optically-detectable carrier, wherein a target for the known binding partner or a binding partner for the known target, if present, is bound or becomes bound to the carrier, to allow the formation of a complex between (1) the carrier-bound target and the known binding partner, or (2) the carrier-bound binding partner and the known target, respectively;
    centrifuging the vessel; and
    observing the location of the carrier to determine the presence of the target antibody or antigen to be detected, with a strongly positive reaction being indicated by the complex lying upon or in a top portion of a layer of the particles, and a negative reaction being indicated by the absence of a complex, with the carrier lying beneath the particles.

2. The method of claim 1, wherein the vessel is mounted on or forms a part of a centrifugable apparatus comprising a planar card member having an identifying indicia-receiving portion and a plurality of said microreaction vessels lying side by side.

3. The method of claim 1, wherein the vessel forms a part of a centrifugable integrated unit comprising a plurality of said microreaction vessels lying side by side.

4. The method of claim 1, wherein the carrier is selected from the group consisting of erythrocytes, leukocytes, platelets, latex particles and polymerized agarose.

5. The method of claim 1, wherein the carrier is erythrocytes.

6. The method of claim 1, wherein in said adding step, about 10–150 μl of the solution is added to the vessel.

7. The method of claim 1, wherein the particles are inert particles.

8. The method of claim 7, wherein the particles are gel particles.

9. The method of claim 1, wherein the particles are gel particles.

10. The method of claim 1, wherein the transition portion of the vessel forms a funnel shape.

11. The method of detecting an analyte antibody or antigen in a fluid sample, the method comprising:
    providing a microreaction vessel containing a slurry or suspension of particles and anti-immunoglobin, wherein the vessel has an upper portion having a sample receiving end and a lower portion having a closed end, the upper portion having a greater diameter or width than the lower portion, with a transition portion situated between the upper portion and the lower portion;
    adding to the vessel the fluid sample which may contain the analyte antibody or antigen;
    adding to the vessel a solution containing an optically-detectable carrier-bound antigen or antibody which is a specific binding partner for the analyte antibody or antigen, respectively, to allow the formation of a complex between (1) the anti-immunoglobin, the carrier-bound antigen and the analyte antibody, or (2) the carrier-bound antibody and the analyte antigen;
    centrifuging the vessel; and
    observing the location of the carrier to determine the presence of the analyte antibody or antigen, with a strongly positive reaction being indicated by the complex lying upon or in a top portion of a layer of the particles, and a negative reaction being indicated by the absence of a complex, with the carrier-bound antigen or antibody lying beneath the particles.

12. The method of claim 11, wherein the vessel is mounted on or forms a part of a centrifugable apparatus comprising a planar card member having an identifying indicia-receiving portion and a plurality of said microreaction vessels lying side by side.

13. The method of claim 11, wherein the vessel forms a part of a centrifugable integrated unit comprising a plurality of said microreaction vessels lying side by side.

14. The method of claim 11, wherein the carrier is selected from the group consisting of erythrocytes, leukocytes, platelets, latex particles and polymerized agarose.

15. The method of claim 11, wherein the carrier is erythrocytes.

16. The method of claim 11, wherein in said adding steps, about 10–150 μl of the fluid sample and about 10–150 μl of the solution are added to the vessel.

17. The method of claim 11, wherein the particles are inert particles.

18. The method of claim 17, wherein the particles are gel particles.

19. The method of claim 11, wherein the particles are gel particles.

20. The method of claim 11, wherein the transition portion of the vessel forms a funnel shape.

21. The method of claim 20, wherein in said adding steps, the fluid sample and the solution contact each other in the transition portion.

22. The method of detecting an analyte antibody in a serum or plasma sample, the method comprising:

providing a microreaction vessel contain a slurry or suspension of particles and anti-immunoglobin, wherein the vessel has an upper portion having a sample receiving end and a lower portion having a closed end, the upper portion having a greater diameter or width than the lower portion, with a funnel-shaped transition portion situated between the upper portion and the lower portion;

contacting with the funnel-shaped transition portion of the vessel (1) the serum or plasma sample which may obtain the analyte antibody and (2) a solution containing an optically-detectable carrier-bound antigen which is a specific binding partner for the analyte antibody, to form a mixture;

incubating the mixture to allow the formation of a complex between the analyte antibody, the carrier-bound antigen and the anti-immunoglobulin;

centrifuging the vessel; and observing the location of the carrier to determine the presence of the analyte antibody, with a strongly positive reaction being indicated by the complex lying upon or in a top portion of a layer of the particles, and a negative reaction being indicated by the absence of a complex, with the carrier-bound antigen lying beneath the particles.

23. The method of claim 22, wherein the vessel is mounted on or forms a part of a centrifugable apparatus comprising a planar card member having an identifying indicia-receiving portion and a plurality of said microreaction vessels lying side by side.

24. The method of claim 22, wherein the vessel forms a part of a centrifugable integrated unit comprising a plurality of said microreaction vessels lying side by side.

25. The method of claim 22, wherein the carrier is selected from the group consisting of erythrocytes, leukocytes, platelets, latex particles and polymerized agarose.

26. The method of claim 22, wherein the carrier is erythrocytes.

27. The method of claim 22, wherein in said contacting step, about 10–150 μl of the serum or plasma sample and about 10–150 μl of the solution are added to the vessel.

28. The method of claim 22, wherein the particles are inert particles.

29. The method of claim 28, wherein the particles are gel particles.

30. The method of claim 22, wherein the particles are gel particles.

* * * * *